US008641620B2

(12) United States Patent
Lasser et al.

(10) Patent No.: US 8,641,620 B2
(45) Date of Patent: Feb. 4, 2014

(54) HAND-HELD ULTRASOUND IMAGING DEVICE AND TECHNIQUES

(75) Inventors: Robert S. Lasser, Washington, DC (US); Marvin E. Lasser, Potomac, MD (US); John P. Kula, Columbia, MD (US)

(73) Assignee: Imperium, Inc., Beltsville, MD (US)

( * ) Notice: Subject to any disclaimer, the term of this patent is extended or adjusted under 35 U.S.C. 154(b) by 1598 days.

(21) Appl. No.: 12/071,521

(22) Filed: Feb. 21, 2008

(65) Prior Publication Data

US 2009/0216129 A1    Aug. 27, 2009

(51) Int. Cl.
*A61B 8/00*    (2006.01)
*A61B 8/14*    (2006.01)

(52) U.S. Cl.
USPC .............. 600/437; 600/446; 600/459

(58) Field of Classification Search
None
See application file for complete search history.

(56) References Cited

U.S. PATENT DOCUMENTS

| 4,131,021 | A | * | 12/1978 | Mezrich et al. | 73/606 |
|---|---|---|---|---|---|
| 4,798,210 | A | * | 1/1989 | Ledley | 600/437 |
| 5,085,221 | A | * | 2/1992 | Ingebrigtsen et al. | 600/446 |
| 5,160,870 | A | * | 11/1992 | Carson et al. | 310/339 |
| 5,212,571 | A | | 5/1993 | Garlick et al. | |
| 5,254,504 | A | * | 10/1993 | Van der Spiegel et al. | 438/3 |
| 5,283,438 | A | | 2/1994 | Dautriche | |
| 5,297,553 | A | * | 3/1994 | Sliwa et al. | 600/459 |
| 5,406,163 | A | | 4/1995 | Carson et al. | |
| 5,483,963 | A | | 1/1996 | Butler et al. | |
| 5,530,678 | A | * | 6/1996 | Kosalos | 367/13 |
| 5,680,863 | A | * | 10/1997 | Hossack et al. | 600/459 |
| 6,014,473 | A | * | 1/2000 | Hossack et al. | 382/294 |
| 6,139,496 | A | * | 10/2000 | Chen et al. | 600/437 |
| 6,206,843 | B1 | * | 3/2001 | Iger et al. | 601/2 |
| 6,511,427 | B1 | * | 1/2003 | Sliwa et al. | 600/438 |
| 6,552,841 | B1 | * | 4/2003 | Lasser et al. | 359/305 |
| 6,776,760 | B2 | * | 8/2004 | Marmarelis | 600/448 |
| 6,835,178 | B1 | * | 12/2004 | Wilson et al. | 600/449 |
| 6,971,991 | B2 | | 12/2005 | Lasser et al. | |
| 7,037,268 | B1 | * | 5/2006 | Sleva et al. | 600/459 |
| 2005/0265267 | A1 | * | 12/2005 | Hwang | 370/310 |
| 2006/0213273 | A1 | | 9/2006 | Lasser et al. | |

* cited by examiner

*Primary Examiner* — Long V. Le
*Assistant Examiner* — Lawrence Laryea
(74) *Attorney, Agent, or Firm* — Buchanan Ingersoll & Rooney PC

(57) ABSTRACT

An acoustic imaging arrangement is disclosed including a longitudinal axis defining an imaging path; a source transducer configured and arranged for producing a beam of acoustic energy, the source transducer comprising a piezoelectric polymer-based material, the source transducer disposed along the imaging path; and at least one sensor disposed along the imaging path, the sensor constructed and arranged to produce electrical signals in response to acoustic energy incident thereon. Related methods are also described.

43 Claims, 7 Drawing Sheets

HAND-HELD ULTRASOUND IMAGING DEVICE AND TECHNIQUES

FIELD

The present invention is in the field acoustic imaging. Also, the present invention is in the field of arrangements and techniques for acoustic imaging that include at least one of a source and a sensor that are formed from a piezoelectric polymer-based material.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

Acoustic imaging, such as ultrasonic imaging, has been used in various material testing or measurement applications. For example, ultrasonic imaging has been used in non-destructive testing applications such as the testing of the properties of manufactured materials (e.g., testing for corrosion in aircraft wings). Acoustic imaging has further been used in medical imaging applications such as human soft tissue diagnosis. Some conventional systems used to perform ultrasonic testing have suffered from a number of disadvantages, such as system complexity and lack of image resolution.

The ultrasonic imaging systems and techniques described in U.S. Pat. No. 6,552,841, the entire contents of which is incorporated herein by reference, represent an advance in the state of the art. The systems and techniques described therein generally include a source transducer, typically formed from a ceramic-based material, which produces an unfocused beam that is then passed through a beam splitter on its way to the target. Both pass-through and reflection modes of operation are described. Thus, the systems and techniques described therein further include a sensor which receives acoustic energy which is either reflected off of, or passed through, the target being imaged.

U.S. Pat. Nos. 5,406,163 and 5,283,438 describe detectors that are formed, at least in part, by a polyvinylidene fluoride material.

Despite the above, there is still a need in the art for improved acoustic imaging arrangements and techniques.

SUMMARY

According to certain aspects, the present invention provides structures, arrangements and techniques that advance the state of the acoustic imaging art.

Thus, according to one aspect, the present invention provides an acoustic imaging arrangement comprising: a longitudinal axis defining an imaging path; a source transducer configured and arranged for producing a beam of acoustic energy, the source transducer comprising a piezoelectric polymer-based material, the source transducer disposed along the imaging path; and at least one sensor disposed along the imaging path, the sensor constructed and arranged to produce electrical signals in response to acoustic energy incident thereon.

According to another aspect, the present invention provides a method of imaging a target using acoustic energy, the method comprising: generating acoustic energy with a source transducer comprising a piezoelectric polymer-based material; directing at least a portion of the beam of acoustic energy such that it is incident upon the target; receiving at least a portion of the incident beam which has been reflected off or passed through the target onto at least one sensor; and producing electrical signals in response to the acoustic energy received upon the at least one sensor.

DETAILED DESCRIPTION

Figure 1:
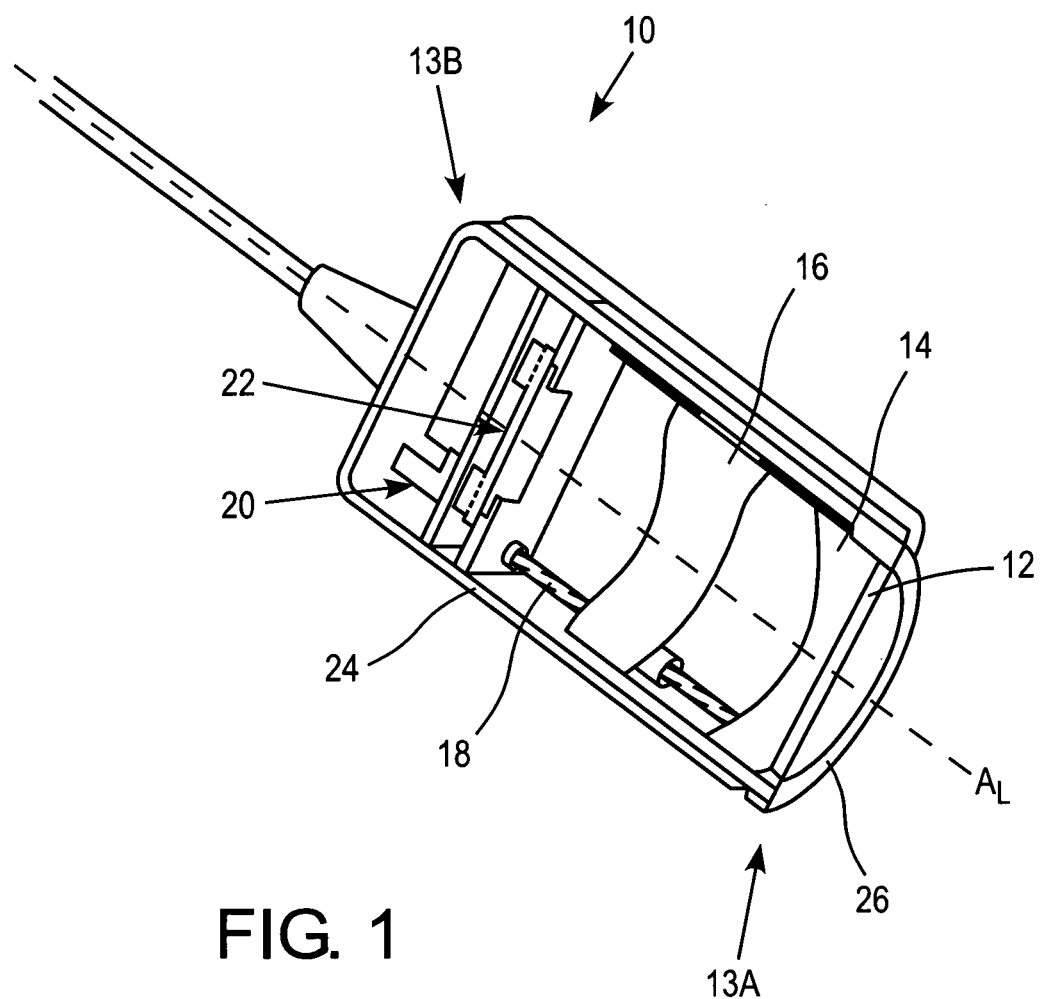
FIG. 1 is a cutaway view of an arrangement formed according to one embodiment of the present invention.
Figure 2:
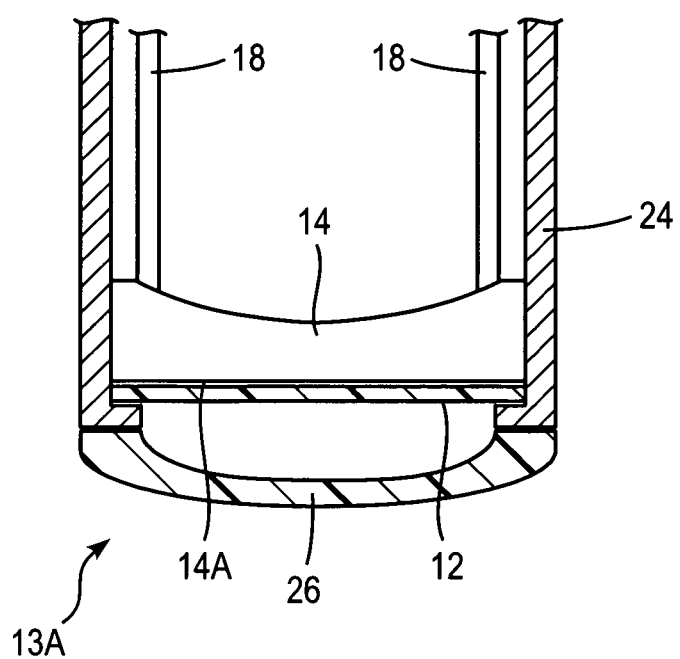
FIG. 2 is a sectional view of a portion of the arrangement of FIG. 1.

According to certain embodiments, the present invention comprises an arrangement of the type illustrated in FIGS. 1-3. As illustrated therein, the arrangement 10 generally comprises, or is centered on, a longitudinal axis $A_L$ which according to the illustrated embodiment also defines an imaging path.

A source transducer 12 for generating acoustic energy is provided. The acoustic energy produced thereby can optionally be in the form of ultrasonic energy. The source transducer 12 is formed from a piezoelectric polymer-containing material. Any suitable piezoelectric polymer-containing material can be utilized. The material should be capable of generating a pulse of acoustic energy in response to an electrical stimulus. As such, the source transducer 12 is in electrical communication with a device which provides an electrical pulse thereto (not shown). The material should also contain a polymer. Thus, composite materials containing a polymeric component are comprehended by the present invention, as are materials which are entirely composed of a polymer. Optionally, the piezoelectric polymer-containing material is flexible and thus conformable to the surface of an object being imaged. According to one illustrative embodiment, the piezoelectric polymer-based containing material comprises polyvinylidene difluoride (PVDF). According to a further embodiment, the piezoelectric polymer-containing material comprises a copolymer of polyvinylidene difluoride, such as a polyvinylidene difluoride-trifluoroethylene (PVDF-TrFE). The source transducer 12 of the present invention is capable of emitting broadband acoustic energy. For example, the source transducer 12 is capable of emitting acoustic energy with a frequency band of 2 MHz-6 MHz. Through material selection and/or physical design, one or more transducers can be provided capable of emitting the above-mentioned band, within a range or spectrum of frequencies from about 0.5 MHz-25 MHz.

According to the illustrated embodiment, the source transducer 12 is positioned proximate to a first longitudinal end 13A of the arrangement 10.

The arrangement 10 may further include at least a first acoustic lens 14, as well as an optional second acoustic lens 16. The first acoustic lens 14 and the second acoustic lens 16, if present, are movably mounted on guides or rails 18 such that their position can be changed along the longitudinal direction. A suitable mechanism, such as a motor 20 can be provided to adjust the longitudinal position of the first acoustic lens 14 and the second acoustic lens 16. According to the present invention, additional lenses may be included in the arrangement 10.

As illustrated, for example, in FIG. 2, the source transducer 12 can be mounted to a surface 14a of the first acoustic lens 14 which is proximate to the first longitudinal end 13A of the arrangement 10.

The first acoustic lens 14 and the second acoustic lens 16, if present, act to focus acoustic energy onto an appropriate sensor 22. The sensor 22 can take any suitable form. For example, the sensor 22 should be able to convert acoustic energy which is incident thereon to electrical signals which can then be utilized to generate an appropriate output, such as an image. That is, acoustic energy incident on the piezoelectric material is converted into electrical signals that can be processed by any subsequent associated circuitry and conventional image processing hardware and/or software. Such image processing hardware and/or software can include conventional data acquisition, digital signal processing, and video/graphics hardware and/or software, such as that disclosed in U.S. Pat. No. 5,483,963, the disclosure of which is incorporated by reference herein in its entirety. According to one embodiment, the sensor 22 may comprise an imaging array. A suitable imaging array can include any number of piezoelectric arrays that are known in the art. An array of PZT detectors, as described in the above-mentioned U.S. Pat. No. 5,483,963, can be used to form an imaging array. As additional examples, arrays of piezoelectric polyvinylidene difluoride (PVDF) polymers described in U.S. Pat. No. 5,406,163 or 5,283,438, the disclosures of which are hereby incorporated by reference in their entirety, can also be used. As illustrated in FIG. 1, the sensor 22 can be located toward a second end 13B of the arrangement, which is opposite to the first end 13A.

Since both the source transducer and sensor of the arrangements of the present invention commonly rely on piezoelectric properties, it is possible to combine the functionality of both the source transducer and sensor into a single component. Thus, for example, with the proper supporting connections and electronics, the thin sheet of piezoelectric polymer-containing material 12 illustrated, for example, in FIG. 2 can function as both a source of acoustic energy, as well as a sensor. When operating as a source, electrical impulses are utilized to produce a mechanical response thereby generating a pulse of acoustic energy. When operating as a sensor, forces incident thereon results in the generation of electrical signals which can be processed and interpreted. The ability to combine source and sensor functionality in a single component obviously provides advantages in terms of simplification, miniaturization, and cost savings. Thus, for example, the piezoelectric polymer containing material 12 can function as a source, as well as a sensor providing feedback that can be used for output during operation in A-scan mode. It is also contemplated that a device of the present invention be operable in both A-scan and C-scan modes simultaneously. Thus, for example, the material 12 can function as a source and receiver providing A-scan output, and the sensor 22 providing signals used to produce C-scan output.

Some or all of the above-described components of the arrangement 10 can be contained within a housing 24. The housing 24 can be formed from any suitable material, such as a polymer. The housing 24 may also be at least partially filled with a fluid which couples the acoustic energy received within the housing 24 to the sensor 22. Any suitable fluid may be utilized, such as water.

As may be best illustrated in FIG. 2, the arrangement 10 may further include a pliable or flexible cover 26 provided at the first end 13A, which can be attached to the housing 24. The flexible cover 26 can be formed from any suitable material, such as a flexible and/or elastic polymer.

Figure 3A:
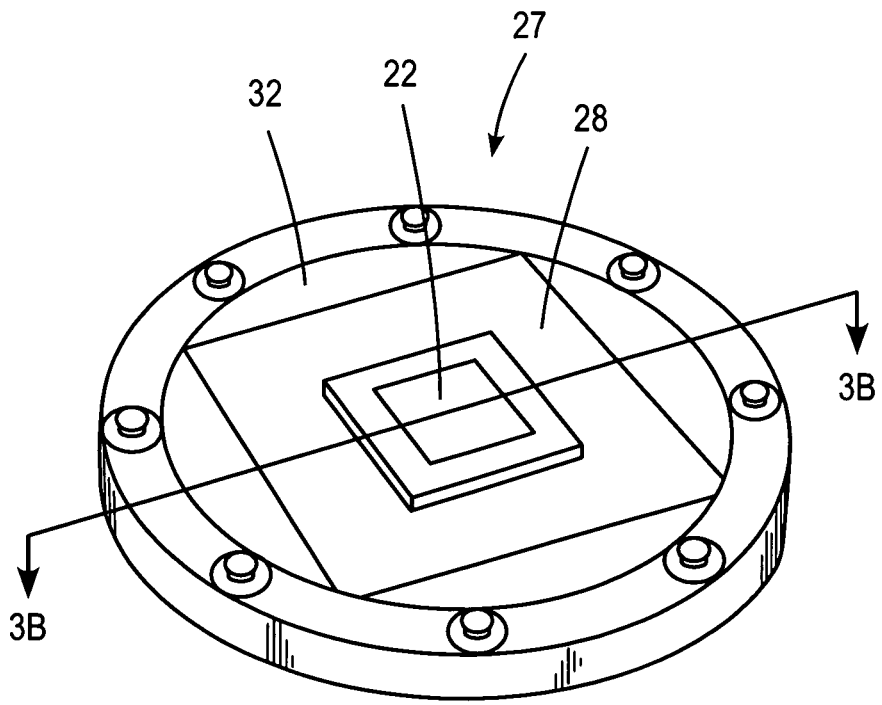
FIGS. 3A-3B are a perspective and a sectional view, respectively, of a portion of the arrangement of FIG. 1.
Figure 3B:
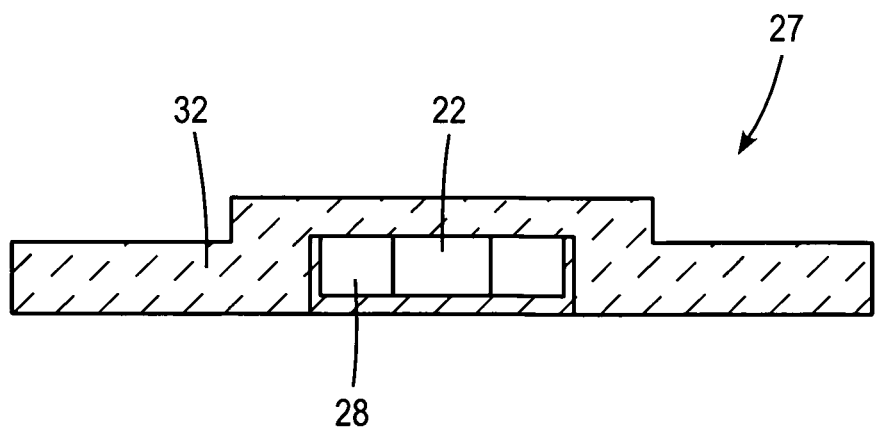

The acoustic energy can be coupled to the sensor 22, via the fluid through an interface. An illustrative, non-limiting interface 27 is shown in FIGS. 3A-3B. As illustrated therein, the sensor 22 can be connected to a substrate or package 28 such as a circuit board. The illustrated interface 27 comprises an encapsulating disk 32. The disk 32 can be comprised of a transparent solid material, such as polycarbonate, RTV silicone and the like, which transmits acoustic energy, but which prevents the coupling fluid within the housing 24 from contacting the sensor 22. The interface 27 therefore couples acoustic energy from the fluid media across the disk 32 and onto the sensor 22.

Figure 4:
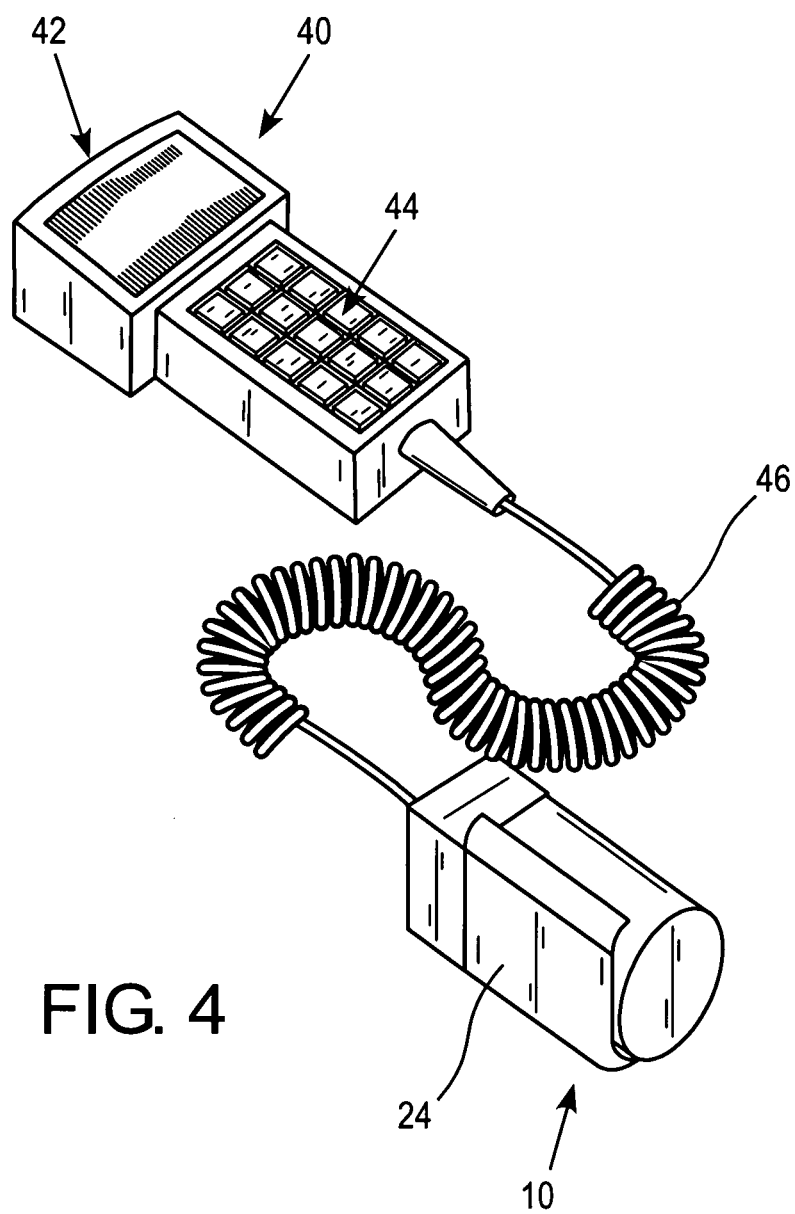
FIG. 4 is a perspective view of an arrangement formed according to a further aspect of the present invention.

As illustrated in FIG. 4, an arrangement formed according to the present invention may further include a second housing 40 which may define an output/control unit which is separate from the components which may be contained within the housing 24. The second housing 40 may contain one or more of an output device 42, such as a display and an input device 44, such as a keypad. The second housing may also contain additional conventional supporting electronics. The first housing 24 and the second housing 40 may be mechanically and/or electrically connected. According to the illustrated embodiment, the first housing 24 and the second housing 40 are both mechanically and electrically connected via a cord 46. It is of course contemplated that the first housing 24 and the second housing 40 may be wirelessly connected. In addition, according to the present invention, output can be wirelessly transmitted to a remote location for viewing and/or analysis.

Electronics that support the function of the source transducer 12 and the sensor 22 can be utilized to "range gate" the acoustic beam that is received at the sensor 22 and its corresponding output. Range gating is the process of controlling two parameters: (1) the time between the acoustic pulse at the source transducer and the time at which sampling of the reflected or transmitted energy begins; and (2) the duration of the delay before sampling begins. A more detailed explanation of range gating, which is not necessary for understanding the principles of the present invention, is set forth in U.S. Pat. No. 6,552,841. The piezoelectric polymer-containing source transducer material of the arrangement of present invention produces a pulse of acoustic energy in two opposite directions therefrom (e.g., a pulse towards the first end 13A and a pulse towards the second end 13B). Thus, a portion of this initial pulse (e.g., the portion transmitted toward the second end 13B) that is incident upon the sensor 22, does not convey any useful information about the object being imaged. According to the principles of the present invention, the above-described range gating technique can be utilized to screen out the readings produced by the sensor from this initial pulse of energy originating from the source transducer, thereby providing output which is representative of acoustic energy which has either been reflected from, or transmitted through, the object being imaged.

Figure 5:
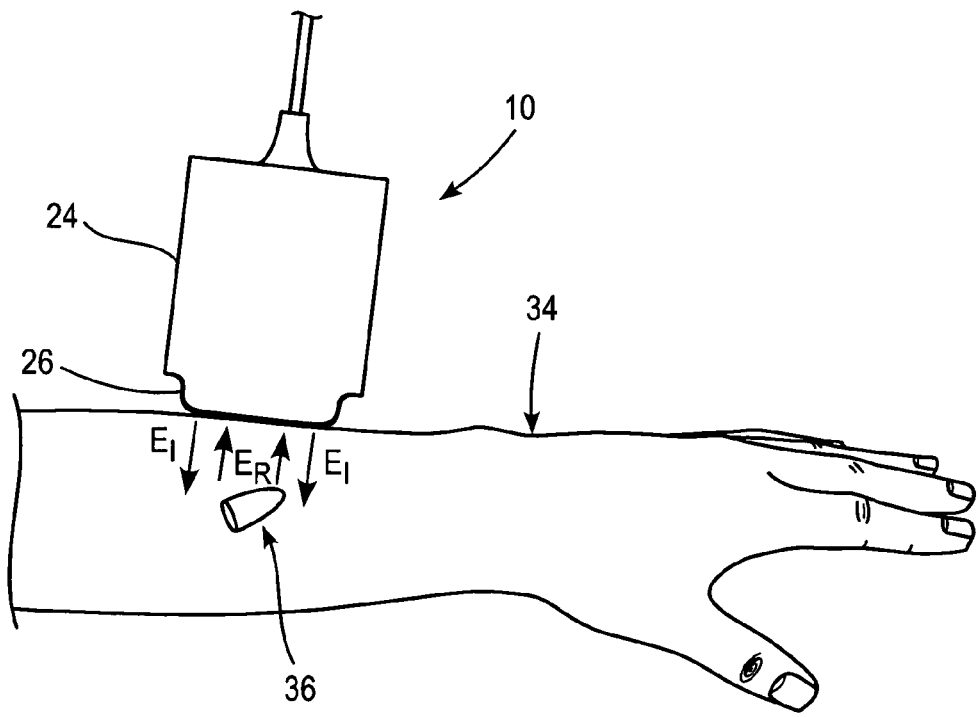
FIG. 5 is a perspective view of an arrangement and mode of operation performed according to the principles of the present invention.

As illustrated in FIG. 5, the arrangement 10 described above can be configured to permit measurement of acoustic energy which is reflected from a target, or in a reflection mode. More specifically, the arrangement 10 is used to image an object 34 by introducing a incident acoustic energy $E_I$ which can be directed toward a target 36 normally hidden from view, and receive acoustic energy reflected therefrom $E_R$. Thus, according to this particular arrangement and mode of operation, the arrangement 10 includes both a source for producing incident acoustic energy $E_I$ as well as an appropriate sensor for receiving and interpreting the reflected acoustic energy $E_R$.

Figure 6:
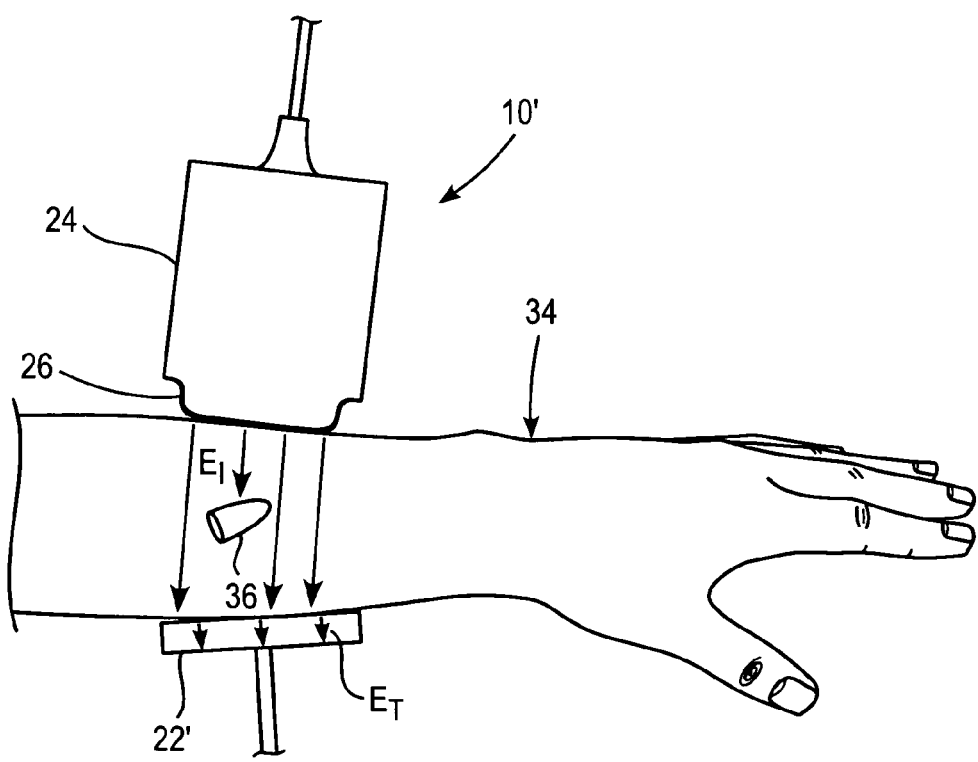
FIG. 6 is a perspective view of an arrangement and mode of operation performed according to further aspects of the present invention.

Alternatively, the arrangement 10 as essentially as described above can be utilized to permit measurement of acoustic energy which has been passed through an object or target, or in a pass-through mode. This arrangement 10' and corresponding mode of operation is illustrated in FIG. 6. As illustrated therein, a separate sensor 22' is provided and positioned to receive acoustic energy $E_I$ which is a first incident on the object 34 and/or target 36, then passed through or transmitted out of the imaged object 34 and/or target 36, as represented by energy ET. The arrangement 10' can have any of the components previously described in connection with the arrangement 10. Obviously, when used exclusively in this mode, it is not necessary to include the sensor 22 within the housing 24. However, the arrangement 10' may also include a sensor 22 within the housing 24, thereby enabling use in either reflection or pass-through a mode. The separate sensor 22' can take any suitable form. For example, the separate sensor 22' can comprise any of the types of sensors previously described here in connection with the discussion of sensor 22 of arrangement 10. The sensor 22' can either be composed a completely separate device from the remainder of the arrangement 10', or can be mechanically and/or electrically connected with the arrangement 10'.

Figure 7:
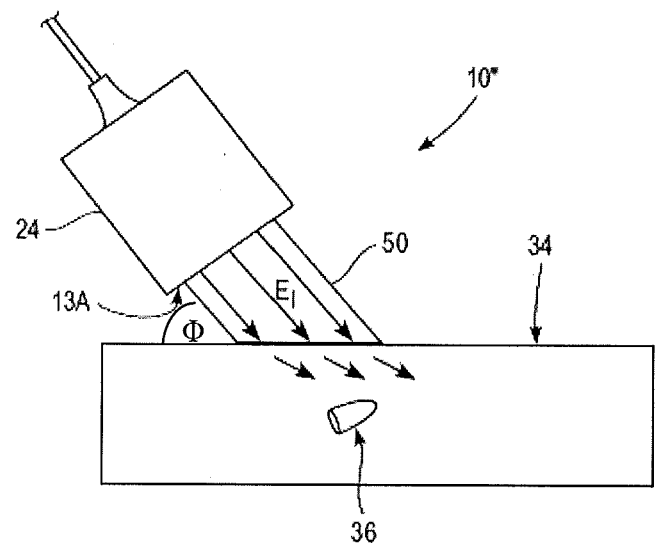
FIG. 7 is a perspective view of an arrangement and mode of operation according to yet another aspect of the present invention.

As illustrated in FIGS. 5-6, the arrangements 10, 10' of the present invention can be utilized in a manner which introduces acoustic energy or waves into the object being imaged that are substantially directed along the longitudinal direction, i.e., substantially parallel to the longitudinal axis of the arrangement $A_L$. However, the present invention is not so limited. Namely, the arrangements 10, 10' formed according to the principles of the present invention can also be utilized in a manner such that a shear acoustic wave is introduced into the object being imaged. This type of arrangement and mode of operation is illustrated, for example, in FIG. 7. As illustrated therein, this modified arrangement 10" is constructed in a manner similar to that of the previously described arrangements, except that a shear wave adapter 50 is provided at the first end 13A. The shear wave adapter 50 causes the incident acoustic energy $E_I$ to enter the object being imaged at an angle Φ which deviates from normal to the surface of the target object 34. According to certain embodiments, the shear wave adapter 50 is adjustable, so that the angle Φ can be varied. Such a shear wave adapter, and this mode of operation, as described in more detail and U.S. Patent Publication No. 2006/0213273, the entire contents of which are incorporated herein by reference.

Figure 8:
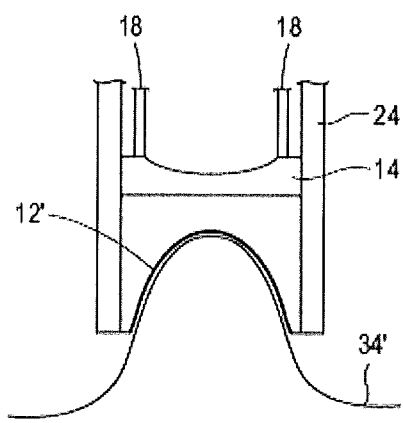
FIG. 8 is a perspective view of an arrangement and mode of operation according to an additional aspect of the present invention.

One of the advantages of utilizing a source transducer and/or sensor formed from piezoelectric polymer-containing material, is the mechanical flexibility of such materials. This enables one to conform the shape of the source transducer and/or sensor to the shape or contour of the object being imaged. For example, as illustrated in FIG. 8, the flexible source transducer 12' is easily conformed to the shape or contour of the object being imaged 34', in this case, a human breast. The ability to conform to the shape of the object being imaged greatly enhances the accuracy of the information derived from the scan. The accuracy of the scan is dependent upon the density of the incident and reflected (or transmitted) energy. The ability to position the source transducer so as to conform to the contours of the object being imaged greatly enhances the ability to both comprehensively introduce and receive energy from multiple angles surrounding the object. It should be understood that the use of such arrangements, including the above-mentioned conformable source transducer/sensor, is equally advantageous in a number of different applications, and thus not limited to breast imaging. It should also be understood that the arrangement depicted in FIG. 7 can include some or all of the above-described components, features and functionality of any of the other arrangements described herein.

Figure 9:
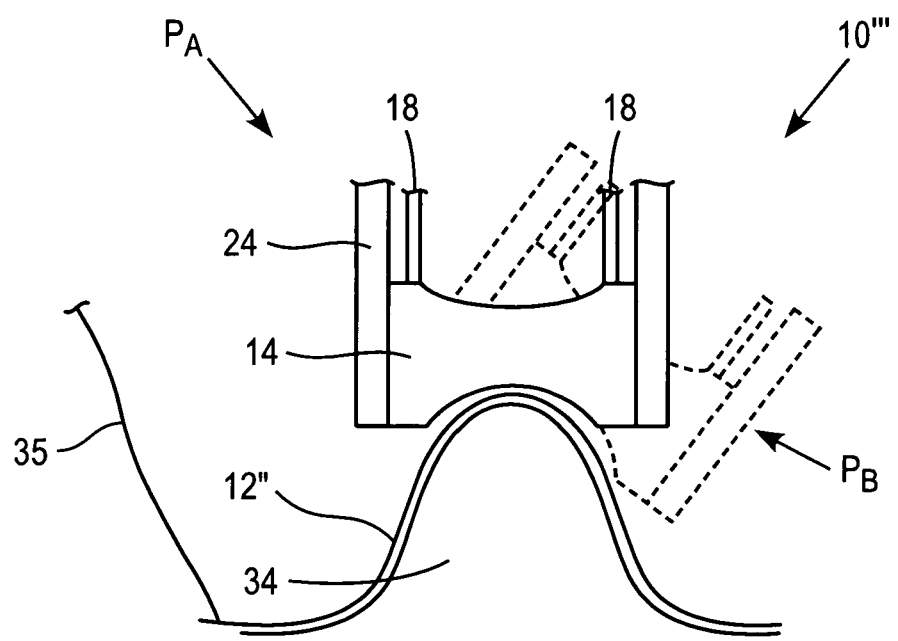
FIG. 9 is a perspective view of an arrangement and mode of operation according to yet another aspect of the present invention.

According to a further alternative, a modified arrangement 10''' can be constructed of the type illustrated in FIG. 9. The arrangement 10''' is similar to the arrangement 10" of FIG. 8, except that the source transducer 12" of arrangement 10" is at least as large as, and preferably larger than, the object being imaged 34. According to this arrangement 10''', the housing 24 is moveable with respect to the source transducer 12", which may also act as a sensor, as in the previous embodiments. Thus, the housing 24, and the components contained therein, can be moved from a first position $P_A$ to a second position $P_B$ to image different portions of the target object 34, which could optionally be a human breast. The source transducer 12" may optionally have an electrical connector 35 that is separate from the electrical connection(s) for those components contained within the housing 24.

Another advantage of arrangements formed according to the principles of the present invention, including the incorporation of the piezoelectric polymer-containing source transducer material disposal in the imaging path, is the ability to omit the inclusion of a beam splitter, which is often included in conventional acoustic imaging arrangements, such as that described in the aforementioned U.S. Pat. No. 6,552,841. Beam splitters can present certain disadvantages and challenges, such as reduction in spatial resolution, typically only effective over a relatively narrow frequency band, and loss of acoustic energy. Thus, according to a further aspect of the present invention, arrangement formed according to the principles of the present invention may optionally omit the inclusion of a beam-splitting device of the type mentioned above in order to avoid the aforementioned is advantages associated therewith.

As alluded to above, according to the present invention, a user can obtain full waveform output using A-scan mode, including depth of a target of interest below the surface of the object being scanned.

The arrangements of the present invention can be used in numerous applications, including the medical diagnosis of human tissue. Using the focus and zoom capabilities of the present invention, the entire depth of human tissue can be scanned. These capabilities are particularly advantageous in breast tissue analysis, where the layers of tissue surrounding a breast mass can be separated. Thus, speculated borders, which are indicative of malignancy of the breast, can more readily be detected. The present invention also provides advantages for guiding core biopsy, cyst drainage and percutaneous tumor ablation. The arrangements of the present invention may additionally can be used to assess the tendons and vessels in the body, such as those of the hands or wrists. The present invention provides delineation of tendons and the bony structures of the fingers and has sufficient penetration of the bones and the fingers that it is feasible to monitor the presence and position of a foreign object, or the placement of surgical pins, in real-time, without x-rays.

When operating in reflection mode, arrangements of the present invention are useful for the non-invasive imaging of objects located under layers of material. Voids, corrosion, delaminations, impact damage, and subsurface cracking are a few of the structural features that can be imaged within a material. The arrangements of the present invention permits the testing of materials with large surface areas, such as large composite or metal sheets, in a fraction of the time of conventional arrangements.

The arrangements of the present invention can be used to obtain an ultrasonic image of a large detection area using C-scan and/or A-scan techniques to obtain an image. For example, the arrangements described herein can be used to obtain an A-scan image of a portion of the large detection area by using first detection signals generated by a first pixel, group of pixels, or portion of the sensor or imaging array. A C-scan image can be obtained by using second detection signals collected from a second group of pixels or second portion of the sensor or imaging array. Such A-scan and C-scan techniques are generally known in the art.

The arrangements of the present invention can additionally be used for underwater detection and identification of mines, subsurface ship salvage, and high resolution imaging in the littoral zone with high resolution. This is in marked contrast to conventional ultrasound side scanning techniques which can detect objects in the ocean, but which have limited resolution. The integrated array, read-out circuitry, and standard video electronics, allows the overall device to be contained within a small package, thus permitting the device to be carried underwater by a diver. This capability to provide high resolution images from a hand-held ultrasonic device currently does not exist.

The present invention is also directed to methods and techniques for acoustic imaging. According to certain embodiments, the methods and techniques associated with the use of the arrangements described herein are encompassed. Generally, a method performed according to the principles of the present invention involves generating acoustic energy with the source transducer comprising a piezoelectric polymer-based material, directing at least a portion of the acoustic energy such that it is incident upon an object to be imaged, receiving at least a portion of the acoustic energy which has been reflected off or passed through the target onto at least one sensor, and producing electrical signals in response to the acoustic energy received upon the least one sensor. The source transducer and sensor can be provided with any suitable construction, including that described previously herein.

As previously explained, a source transducer formed according to the present invention, when stimulated by a pulse electricity, generates a wave of acoustic energy which propagates in opposing directions from the surface thereof. The portion of this initial wave of acoustic energy which is emitted toward and captured by the sensor can be range-gated out such that the signals produced thereby are not figured into the output. This is because the signals produced by this initial wave of acoustic energy received upon the sensor are not indicative of any of the properties of an object to be imaged.

As further explained herein, a method performed according to the principles of the present invention can utilize the same piece of piezoelectric polymer-based material to act as both the source transducer and sensor.

All numbers expressing measured values, quantities, constituents, reaction conditions, and so forth used in the specification are to be understood as being modified in all instances by the term "about." Notwithstanding that the numerical ranges and parameters set forth, the broad scope of the subject matter presented herein are approximations, the numerical values set forth are indicated as precisely as possible. Any numerical value, however, may inherently contain certain errors resulting, for example, from their respective measurement techniques, as evidenced by standard deviations associated therewith. Also, recitations contained herein are not intended to be construed as mean-plus-function limitations under 35 U.S.C. §112, ¶6 unless the term "means" is expressly associated therewith.

Although the present invention has been described in connection with preferred embodiments thereof, it will be appreciated by those skilled in the art that additions, deletions, modifications, and substitutions not specifically described may be made without departing from the spirit and scope of the invention.

We claim:

1. An acoustic imaging arrangement comprising:
   a longitudinal axis defining an imaging path;
   a source transducer configured and arranged for producing a beam of acoustic energy, the source transducer comprising a piezoelectric polymer-based material, the source transducer disposed along the imaging path;
   at least one sensor disposed along the imaging path, the sensor constructed and arranged to produce electrical signals in response to reflected acoustic energy incident thereon; and
   wherein the source transducer is configured to direct the beam of acoustic energy along the imaging path so that at least a portion of the beam of acoustic energy reflected by an object, during operation, passes through the source transducer before reaching the sensor.

2. The arrangement of claim 1, further comprising a housing, and the source transducer, at least one acoustic lens, and the at least one sensor are arranged within the housing.

3. The arrangement of claim 2, wherein the housing contains a fluid which is transmissive to acoustic energy.

4. The arrangement of claim 3, wherein the fluid comprises water.

5. The arrangement of claim 2, further comprising a second housing configured and arranged to receive and/or send signals with the first housing.

6. The arrangement of claim 5, wherein the second housing contains at least one of: a display and a mechanism for inputting commands to be sent to the first housing.

7. The arrangement of claim 5, wherein the signals are transmitted between the first and second housing via a wired or wireless connection.

8. The arrangement of claim 2, wherein the source transducer is configured and arranged to transmit the beam of acoustic energy produced thereby from the arrangement without first passing through the at least one acoustic lens.

9. The arrangement of claim 1, wherein the polymer-based material comprises polyvinylidene difluoride.

10. The arrangement of claim 1, wherein the polymer-based material comprises a copolymer of polyvinylidene difluoride.

11. The arrangement of claim 1, wherein the arrangement comprises a first end formed at least in part from a flexible material.

12. The arrangement of claim 11, wherein the at least one source transducer is located proximate to the first end.

13. The arrangement of claim 12, the arrangement further comprising at least one acoustic lens disposed along the imaging path constructed and arranged to focus acoustic energy upon the at least one sensor, the at least one source transducer is mounted to a surface of the at least one acoustic lens.

14. The arrangement of claim 1, wherein the at least one source transducer emits acoustic energy with a wavelength of about 0.5 MHz-25 MHz.

15. The acoustic imaging arrangement of claim 14, wherein the wavelength of the acoustic energy is about 2 MHz-6 MHz.

16. The arrangement of claim 1, wherein the arrangement comprises a plurality of acoustic lenses in series along the imaging path.

17. The arrangement of claim 16, wherein the acoustic lenses are movably mounted within a housing such that a longitudinal position of the acoustic lenses along the imaging path can be changed.

18. The arrangement of claim 1, wherein the arrangement does not include a beam splitter.

19. The arrangement of claim 1, wherein the sensor includes a piezoelectric polymer-based material.

20. The arrangement of claim 1, wherein the at least one source transducer is provided with a non-planar shape that conforms to a shape of the object being imaged.

21. The arrangement of claim 1, wherein the at least one sensor comprises an imaging array.

22. The arrangement of claim 21, wherein the imaging array comprises a two-dimensional array of acoustic to electrical transducers which produce electrical signals in response to acoustic energy incident thereon.

23. The arrangement of claim 1, wherein the at least one sensor comprises a sheet of piezoelectric polymer-based material disposed along the imaging path.

24. The arrangement of claim 1, further comprising a shear wave adaptor provided at a first end of the housing.

25. The arrangement of claim 1, wherein the arrangement is constructed to provide both A-scan and C-scan output.

26. The arrangement of claim 25, wherein the A-scan and C-scan output is provided simultaneously.

27. The arrangement of claim 1, further comprising:
a housing having a first end defining a first area; and
the source transducer defining a second area;
wherein the second area is larger than the first area; and
wherein the housing and the source transducer are relatively moveable.

28. The arrangement of claim 1, wherein the source transducer is flexible such that the source transducer can be conformed to a shape or contour of an object being imaged.

29. The arrangement of claim 1, wherein the source transducer and the at least one sensor are disposed at different locations along the longitudinal axis.

30. The acoustic imaging arrangement of claim 1, wherein the sensor comprises an array of detectors.

31. The acoustic imaging arrangement of claim 30, wherein at least one of the detectors comprises PZT.

32. The acoustic imaging arrangement of claim 1, wherein the sensor comprises polyvinylidene difluoride.

33. A method of imaging a target using acoustic energy, the method comprising:
generating acoustic energy with a source transducer comprising a piezoelectric polymer-based material;
directing at least a portion of the beam of acoustic energy such that the portion of the beam of acoustic energy is incident upon the target, reflects off the target, and then passes through the source transducer;
receiving the portion of the beam of acoustic energy, which has reflected off the target and passed through the source transducer, onto the at least one sensor; and
producing electrical signals in response to the acoustic energy received upon the at least one sensor.

34. The method of claim 33, wherein the source transducer generates acoustic energy emitting from the source transducer in opposing longitudinal directions therefrom, the admitted acoustic energy traveling toward the target in a first longitudinal direction, and toward the least one sensor in a second opposing longitudinal direction.

35. The method of claim 34, further comprising disregarding electrical signals produced by the acoustic energy emitted in the second longitudinal direction and incident upon the least one sensor.

36. The method of claim 34, wherein the source transducer and the at least one sensor are disposed at different locations along the longitudinal axis.

37. The method of claim 33, wherein the acoustic energy is generated and received after being reflected off or passed through the target by the same piece of piezoelectric polymer-based material.

38. The method of claim 33, wherein the polymer-based material comprises polyvinylidene difluoride.

39. The method of claim 33, wherein the polymer-based material comprises a copolymer of polyvinylidene difluoride.

40. The method of claim 33, comprising producing output based on the electrical signals, and wirelessly transmitting the output to a remote location for at least one of observation and analysis.

41. The method of claim 33, further comprising conforming the source transducer to a shape or contour of the target.

42. The method of claim 33, comprising transmitting the acoustic energy generated by the source transducer toward the target without passing the energy through a lens.

43. The method of claim 33, further comprising positioning the source transducer between the target and the at least one sensor.

* * * * *